US010201410B2

(12) United States Patent
Lv et al.

(10) Patent No.: US 10,201,410 B2
(45) Date of Patent: Feb. 12, 2019

(54) HIGH-STRENGTH BIOLOGICAL SCAFFOLD MATERIAL AND PREPARATION METHOD THEREOF

(71) Applicants: SOOCHOW UNIVERSITY, Jiangsu (CN); SILK PLUG (BEIJING) BIOMEDICINE TECHNOLOGY COMPANY LIMITED, Beijing (CN)

(72) Inventors: Qiang Lv, Jiangsu (CN); Zheng Luo, Beijing (CN)

(73) Assignees: SOOCHOW UNIVERSITY, Jiangsu (CN); SILK PLUG (BEIJING) BIOMEDICINE TECHNOLOGY COMPANY LIMITED, Beijing (CN)

(*) Notice: Subject to any disclaimer, the term of this patent is extended or adjusted under 35 U.S.C. 154(b) by 169 days.

(21) Appl. No.: 15/064,925

(22) Filed: Mar. 9, 2016

(65) Prior Publication Data

US 2016/0184069 A1 Jun. 30, 2016

Related U.S. Application Data

(62) Division of application No. 13/981,256, filed as application No. PCT/CN2011/081550 on Oct. 31, 2011.

(30) Foreign Application Priority Data

Jan. 27, 2011 (CN) .......................... 2011 1 0029805

(51) Int. Cl.
*A61F 2/00* (2006.01)
*A61L 27/22* (2006.01)
(Continued)

(52) U.S. Cl.
CPC ...... *A61F 2/0009* (2013.01); *A61B 17/12031* (2013.01); *A61L 27/227* (2013.01); *A61L 27/34* (2013.01); *A61L 27/56* (2013.01)

(58) Field of Classification Search
None
See application file for complete search history.

(56) References Cited

U.S. PATENT DOCUMENTS

| 5,769,884 A * | 6/1998 | Solovay | A61F 2/07 606/194 |
| 6,589,257 B1 * | 7/2003 | Shimizu | A61L 27/24 606/152 |

(Continued)

FOREIGN PATENT DOCUMENTS

| CN | 1736352 A | 2/2006 |
| CN | 1895687 A | 1/2007 |

(Continued)

OTHER PUBLICATIONS

Nazarov, Rina et al. "Porous 3-D Scaffolds from Regenerated Silk Fibroin" Biomacromolecules, 2004, 5, 718-726.*

(Continued)

*Primary Examiner* — Matthew J Daniels
*Assistant Examiner* — Mohammad M Ameen
(74) *Attorney, Agent, or Firm* — Perne & Gordon LLP

(57) ABSTRACT

A high-strength biological scaffold and preparation method thereof. The biological scaffold is comprised of a framework of boiled-off silk woven material, the form of the framework is determined by actual needs; the framework surface is coated with a layer of silk protein scaffold material, fibroin protein/gelatin biological scaffold material or fibroin protein/collagen biological scaffold material having a thickness of 100 micrometers to 5 centimeters. The high-strength biological scaffold material has high tear resistance strength and mechanical strength and good biocompatibility, has a porous structure suitable for tissue regeneration, and can be used for preparing anal fistula repair plugs.

4 Claims, 2 Drawing Sheets

(51) Int. Cl.
*A61L 27/34* (2006.01)
*A61L 27/56* (2006.01)
*A61B 17/12* (2006.01)

(56) References Cited

U.S. PATENT DOCUMENTS

2011/0009960 A1* 1/2011 Altman ................ A61F 2/0059
  623/8
2011/0224703 A1* 9/2011 Mortarino ............ A61F 2/0063
  606/151
2011/0244703 A1 10/2011 Wang et al.

FOREIGN PATENT DOCUMENTS

| CN | 101195043 A | 6/2008 |
| CN | 102091349 A | 6/2011 |
| EP | 2210971 A1 | 7/2010 |

OTHER PUBLICATIONS

International Search Report for PCT/CN2011/081550 dated Feb. 23, 2012.

* cited by examiner

HIGH-STRENGTH BIOLOGICAL SCAFFOLD MATERIAL AND PREPARATION METHOD THEREOF

This application is a divisional of application Ser. No. 13/981,256 filed Jul. 23, 2013, which is incorporated herein by reference in its entirety.

FIELD OF INVENTION

The present invention relates to a method for preparing biological scaffolds, particularly relates to a high-strength biological scaffold material having a porous structure suitable for tissue regeneration, prepared using silk fibroin as a raw material. This biological scaffold material can be specifically used to prepare anal fistula repair plug. It can be applied not only to the treatment of anal fistula disease, but also to repair of both intestinal fistula and other tissue defects.

BACKGROUND OF THE INVENTION

Anal fistula is a common anorectal disease, accounting for 1.6-3.6% of anorectal diseases, and usually formed by rupture or incision of anorectal abscess. Compared with other diseases, anal fistula is characterized in extreme pain in patients, low surgical success rate, and probable recurrence, bringing about tremendous physical and psychological problems to the patients. Anal fistula treatment mainly comprises surgical incision, hanging line therapy, anal fistula excision, cryotherapy, and electrotherapy, etc. These treatments suffer from the defects of extreme pain during treatment, low cure rate (lower than 40%), long recovery period, and frequent recurrence. In recent years, based on findings in tissue engineering study, the use of biocompatible scaffolds for anal fistula repair bring a new dawn to the treatment of anal fistula. Compared with the traditional treatment methods, scaffold repair surgery has the advantages of reduced pains, improved success rate, fewer complications, lower recurrence rate, and has been generally accepted by patients in developed countries. In the current clinical trials, the prosthetic materials mainly used include fibrin gels and porcine small intestinal submucosa scaffold developed by Cook Medical, Inc. Among them, fibrin gels degrade rapidly, and yield an anal fistula cure rate of below 40%. Compared with fibrin gels, porcine small intestinal submucosa scaffold has improved degradation rate, and yields an increased anal fistula cure rate to about 50%. Nevertheless, its degradation rate still cannot fully meet the requirements of the treatment of anal fistula, and resulted in an anal fistula recurrence rate of 10% or greater. Moreover, it suffers from complex extraction and preparation process, high cost, and high price of around $2,000 each, which is unbearable to patients in China Thus, the treatment of anal fistula is urgent for the latest results in the tissue engineering studies, so as to develop new porous scaffolds having good biocompatibility, high mechanical strength, low degradation rate, and low price.

Silk fibroin is the main component of silk, which is inexpensive and easy to purify. Studies have shown that silk fibroin is non-toxic, non-immunogenic, well biocompatible, biodegradable, and excellent in mechanical properties. It is an ideal raw material for the preparation of tissue repair and tissue engineering scaffolds. Silk fibroin has different crystal structure including Silk I and Silk II. The difference in types and contents of crystals can determine the solubility and degradation of silk fibroin. By adjusting its crystal and non-crystal structure, the in vivo degradation rate of silk fibroin can be reduced from one year to about half a month, so as to meet the different needs of tissue repair and regeneration.

Currently, researchers have developed various methods for preparation of silk fibroin scaffolds, comprising a freeze-drying method, a phase separation method, a salting-out method and an electrostatic spinning method, etc. However, the above methods each have deficiencies difficult to overcome. For example, a silk fibroin scaffold prepared by salting-out typically has a pore size of 400 microns or more, and a porous material prepared by electrostatic spinning typically has a pore size of 100 microns or less. As such, there are restrictions for their use as a tissue repair or tissue engineering scaffold. A porous scaffold having a larger range of pore size can be prepared by freeze-drying. However, during the freezing process, the silk fibroin is liable to be self-assembled into a sheet structure, and it is difficult to obtain a good porous structure. In the prior art, a porous scaffold having a good pore structure and suitable for tissue growth has been successfully prepared by controlling the self-assembly of silk fibroin. However, the scaffold thus obtained faces a major problem in practical applications. It has relatively poor mechanical strength and weak tearing resistance, and therefore is difficult to be sutured and fixed by a surgical thread or to be operated by minimally invasive surgical operation, which results in that the scaffold cannot be practically used in clinical application, especially in anal fistula repair plugs.

Therefore, there is a need to overcome the above problems in the prior art, to develop a high-strength biological scaffold material having high tear resistance strength and suitable to be sutured and fixed by a surgical thread, and thereby to prepare a fibroin anal fistula repair plug in order to meet the practical needs.

SUMMARY OF THE INVENTION

The present invention is aimed at providing a high strength biological scaffold material and method for preparation thereof, by improving the mechanical strength and tear resistance of silk fibroin-based scaffold in order to meet the practical needs.

In order to achieve the above purpose, the invention provides the following technical solution: a high-strength biological scaffold material, characterized in that, said high-strength biological scaffold material is comprised of a coating layer and a framework, said framework is embedded in the coating layer; said framework is a boiled-off silk woven material, the weave density can be determined by needs; the coating layer has a thickness of 100 microns to 5 cm, and the material of the coating layer is selected from the group consisting of: silk protein scaffold material, silk fibroin/gelatin biological scaffold material or silk fibroin/collagen biological scaffold material.

In the above embodiment, the weave density of the boiled-off silk woven material is such that the distance between adjacent boiled-off silks is between 0.5 mm and 3 mm. For example, the distance between two adjacent warp boiled-off silks is 0.5 mm to 3 mm, and the distance between two adjacent weft boiled-off silks is 0.5 mm to 3 mm. A suitable weave density can ensure both high tear resistance of the material and suitable porosity, and is beneficial to tissue repair and regeneration.

In the above embodiment, preferably, the coating layer has a thickness of 100 microns to 5 mm; and the high-strength biological scaffold material has a pore size of 200 to 400 microns, and a porosity of 80% or more.

A method for preparing the above high-strength biological scaffold material comprises the following steps: boiled-off silk obtained by degumming silk is woven into a woven material by a textile machine to form a framework according to the desired shape, and then the framework is placed into a mold; a solution containing silk fibroin is injected into the mold having the framework placed therein, and subjected to freezing and vacuum treatment; thereby a coating layer having a thickness of 100 microns to 5 cm is formed on the surface of the framework, and the high-strength biological scaffold material is prepared, wherein said solution containing silk fibroin is one selected from the group consisting of: an aqueous silk fibroin solution, a mixed solution of silk fibroin and gelatin, and a mixed solution of silk fibroin and collagen; the weave density of the woven material is such that the distance between adjacent boiled-off silks is between 0.5 mm and 3 mm, and the material of the coating layer is selected from the group consisting of: silk protein scaffold material, silk fibroin/gelatin biological scaffold material or silk fibroin/collagen biological scaffold material.

In the above embodiment, the step of coating the surface of the framework with a coating layer comprises the specific steps of:
1) preparing a solution containing silk fibroin, the solution containing silk fibroin being one selected from the group consisting of: an aqueous silk fibroin solution, a mixed solution of silk fibroin and gelatin, and a mixed solution of silk fibroin and collagen; injecting the solution containing silk fibroin into the mold having the framework placed therein, and subjecting it to freezing under a low temperature of −10 to −80° C. for 1 to 24 hours to obtain frozen crystals; freeze-drying the frozen crystals to obtain a composite material, the composite material having boiled-off silk woven material as a framework and a layer of soluble silk fibroin layer/silk fibroin and gelatin composite layer/silk fibroin and collagen composite layer coated on the framework;
2) placing the composite material obtained in step 1) into a vacuum dryer and performing a vacuum treatment for 20 minutes to 24 hours to obtain a water-insoluble composite high-strength biological scaffold material, the composite high-strength biological scaffold material having boiled-off silk woven material as a framework and a coating layer provided on the framework, the material of the coating layer being selected from the group consisting of: silk protein scaffold material, silk fibroin/gelatin biological scaffold material or silk fibroin/collagen biological scaffold material; and the vacuum dryer containing water, aqueous methanol or aqueous ethanol at the bottom thereof.

In the above embodiment, in step 1), the aqueous silk fibroin solution is prepared by: subjecting silk to degumming, dissolution, and dialysis to obtain a silk fibroin solution, the aqueous silk fibroin solution having a mass concentration of 0.1 to 20%; leaving the aqueous silk fibroin solution at 0 to 80° C. for 1 to 48 hours;

In the above embodiment, in step 1), the mixed solution of silk fibroin and gelatin is prepared by: preparing an aqueous gelatin solution by adding medical gelatin into distilled water, heating to obtain an aqueous gelatin solution, and leaving the solution at 0 to 10° C. for 30 minutes to 2 hours, the aqueous gelatin solution having a mass concentration of 0.01 to 20%; then mixing an aqueous silk fibroin solution with the aqueous gelatin solution at a mass ratio of silk fibroin to gelatin of 100:2 to 20, to obtain the mixed solution of silk fibroin and gelatin;

In the above embodiment, in step 1), the mixed solution of silk fibroin and collagen is prepared by: preparing an aqueous silk fibroin solution by subjecting silk to degumming, dissolution, and dialysis to obtain a silk fibroin solution, the aqueous silk fibroin solution having a mass concentration of 0.1 to 20%; leaving the aqueous silk fibroin solution at 0 to 80° C. for 1 to 48 hours; preparing a solution of collagen in acetic acid at a concentration of 0.01% to 2%, and leaving the solution at 0 to 10° C. for 30 minutes to 2 hours; then mixing the aqueous silk fibroin solution with the solution of collagen in acetic acid at a mass ratio of silk fibroin to collagen of 100:2 to 20, to obtain the mixed solution of silk fibroin and collagen.

In the above embodiment, preferably, the desired shape can be tubular, cylindrical, or conical.

In the above embodiment, preferably, in step 2), the aqueous methanol has a volume concentration of 1 to 100%; and the aqueous ethanol has a volume concentration of 1 to 100%.

The instant application also claims a method for preparing a high-strength anal fistula repair plug, characterized in that, the method comprises the following steps:
1) preparing a solution containing silk fibroin, the solution containing silk fibroin being one selected from the group consisting of: an aqueous silk fibroin solution, a mixed solution of silk fibroin and gelatin, and a mixed solution of silk fibroin and collagen;
2) weaving degummed boiled-off silk into a tubular material to provide a framework and placing the tubular material into a mold for preparing anal fistula repair plug, the weave density of the tubular material being such that the distance between adjacent boiled-off silks is between 0.5 mm and 3 mm;
3) injecting the solution containing silk fibroin into the mold having the tubular material placed therein, and subjecting it to freezing under a low temperature of −10 to −30° C. for 20 to 24 hours to obtain a frozen body; freeze-drying the frozen body to obtain a soluble composite anal fistula repair plug, the soluble composite anal fistula repair plug having the tubular material woven from boiled-off silk as a framework and a layer of soluble silk fibroin layer/silk fibroin and gelatin composite layer/silk fibroin and collagen composite layer coated on the framework;
4) placing the soluble composite anal fistula repair plug into a vacuum dryer and performing a vacuum treatment for 4 hours or more to obtain a water-insoluble composite anal fistula repair plug, the water-insoluble composite anal fistula repair plug having the tubular material woven from boiled-off silk as a framework and a biological scaffold material as a coating layer, the biological scaffold material being selected from the group consisting of: silk protein biological scaffold material, silk fibroin/gelatin biological scaffold material or silk fibroin/collagen biological scaffold material, the framework being embedded inside the coating layer; and the vacuum dryer containing water, aqueous methanol or aqueous ethanol at the bottom thereof.

In the above embodiment, in step 1), the aqueous silk fibroin solution is prepared by: preparing an aqueous silk fibroin solution having a mass concentration of 0.5% to 5% by a conventional method, and leaving the aqueous silk fibroin solution at 0 to 10° C. for 30 minutes or more;

In the above embodiment, in step 1), the mixed solution of silk fibroin and gelatin is prepared by: preparing an aqueous gelatin solution having a mass concentration of 0.05% to 1%, and leaving the solution at 0 to 10° C. for 30 minutes to 2 hours; mixing an aqueous silk fibroin solution with the aqueous gelatin solution uniformly such that the mass concentration of silk fibroin is 0.2% to 3% and the mass concentration of gelatin is 0.02% to 0.2% upon mixing; and leaving the mixture stand for 4 to 10 hours to obtain the mixed solution of silk fibroin and gelatin;

In the above embodiment, in step 1), the mixed solution of silk fibroin and collagen is prepared by: preparing a solution of collagen in acetic acid at a concentration of 0.05% to 1%, and leaving the solution at 0 to 10° C. for 30 minutes to 2 hours; mixing an aqueous silk fibroin solution with the solution of collagen in acetic acid uniformly at 0 to 10° C. such that the mass concentration of silk fibroin is 0.2% to 3% and the mass concentration of collagen is 0.02% to 0.2% upon mixing; and leaving the mixture stand for 4 to 10 hours to obtain the mixed solution of silk fibroin and collagen.

In the above embodiment, preferably, in step 1), the aqueous silk fibroin solution has a mass concentration of 0.1% to 2%; the aqueous gelatin solution or the solution of collagen in acetic acid has a mass concentration of 0.075% to 0.2%; when mixing an aqueous silk fibroin solution with the aqueous gelatin solution or the solution of collagen in acetic acid uniformly, the aqueous silk fibroin solution is mixed with the aqueous gelatin solution or the solution of collagen in acetic acid in equal volume.

In the above embodiment, preferably, in step 4), the coating layer has a thickness of 100 microns to 5 mm; and the silk fibroin/gelatin or collagen biological scaffold material has a pore size of 200 to 400 microns, and a porosity of 80% or more.

The instant application also claims a composite anal fistula repair plug prepared by the method of the above embodiments, having a tubular material woven from boiled-off silk as a framework and a biological scaffold material as a coating layer, the framework being embedded inside the coating layer, the biological scaffold material being selected from the group consisting of: silk protein biological scaffold material, silk fibroin/gelatin biological scaffold material or silk fibroin/collagen biological scaffold material, and the biological scaffold material having intercommunicated pores with a pore size of 10 to 1000 microns, and a porosity of 80% or more.

In the above embodiment, preferably, the biological scaffold material having intercommunicated pores with a pore size of 150 to 450 microns, and a porosity of 90% or more; wherein the porosity is defined as the volume percentage of the volume of pores inside a porous solid material such as bricks, rocks, steel, silicon, etc., based on the total volume of the material, representing how many pores are contained in the material.

The anal fistula repair plug has adjustable crystal structure and composition, as well as adjustable degradation rate.

The present invention is based on the following principles. Silk fibroin undergoes a slow self-assembly process in an aqueous solution, can gradually be self-assembled into nanospheres or further assembled into nanowires from scattered molecules. Once successfully assembled, silk fibroin can remain stable for a relatively longer time, and can be stable in an aqueous solution. This self-assembly process can be affected by temperature, hydrophilic and hydrophobic interactions, concentration of the solution, ionic strength, pH, and time, etc. As such, the microstructure of silk fibroin can be adjusted by adjusting various simple physical factors, thereby controlling the formation of the porous structure. It should be noted that, none of the silk fibroin porous materials prepared by any method previously known has mechanical properties that can substantially meet the practical requirements of clinical surgery, and they are urgent for improved mechanical strength, especially tear resistance. Boiled-off silk is a silk fibroin fiber obtained by removing sericin from the surface of silk. It has excellent mechanical strength and tear resistance. In the present invention, the boiled-off silk is woven and incorporated, as a framework, into the silk fibroin-based anal fistula repair plug. The problem of poor mechanical strength of the silk fibroin porous materials is thereby effectively solved. Finally, the present invention provides a post-processing method which successfully prepares silk fibroin porous scaffolds having different crystal compositions by treating the silk fibroin scaffolds in a vacuum environment with saturated water, methanol, ethanol and the like. Thus, the invention achieves controllable degradation of silk fibroin porous scaffolds while effectively reduced or eliminated the use of toxic solvents.

The present invention provides the following advantages over the prior art, due to the use of the above technical solutions.

1) The present invention utilizes tubes woven from biocompatible boiled-off silk as the framework of the porous anal fistula repair plug, and significantly improves the mechanical strength of the material, to meet the specific requirements in clinical repair plug applications.

2) The porous scaffold obtained according to the present invention has intercommunicated pores with a pore size of 10 to 1000 microns, which is suitable for cell adhesion and growth. Thus, the biocompatibility is significantly improved, which is beneficial for tissue repair and tissue engineering applications. Moreover, the secondary structure of silk fibroin can be effectively regulated by different post treatments, thereby imparting different degradation properties to meet the different needs of anal fistula repair. The whole preparation process does not require addition of any chemical cross-linking agent or foaming agent, and the good biocompatibility of the silk fibroin is effectively maintained.

3) Since it is conducted below room temperature and in an aqueous environment, the preparation process is mild and easy to control, and does not result in reduced biocompatibility of silk fibroin.

4) In the preparation process, the size of the ice crystals can be controlled by adjusting parameters such as the freezing temperature or the concentration of the solution. Thus, the purpose of controlling the structure of the porous scaffold can be conveniently achieved, so as to meet different application requirements.

5) In the post treatment process, the crystal structure of the prepared silk fibroin porous scaffold can be effectively controlled by changing the processing solution, so as to achieve the purpose of controlling the degradation rate thereof.

DETAILED EMBODIMENTS

Next, the present invention is further described by the aid of drawings and examples.

Example 1

In this example, the silk fibroin porous scaffold is prepared according to the following steps:
1) 5 g of cocoons are added to 2 liters of a sodium carbonate solution having a mass concentration of 0.5%, treated at 98 to 100° C. for 40 min to remove the external sericin, and sufficiently washed to obtain pure silk fibroin.
2) The degummed silk fibroin (also referred to as "boiled-off silk") is woven into a tubular material having a diameter of 4 mm by a textile machine to form a framework, the weave density of the material is such that the distance between adjacent warp boiled-off silks is about 1 mm, and the distance between adjacent weft boiled-off silks is about 1 mm. The tubular material is placed into a repair plug mold having a diameter of 5 mm.
3) The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.
4) The mass concentration of the silk fibroin is adjusted to 4%, and the aqueous solution is placed at 4° C. for 1 hour, such that the solution temperature is stably maintained at 4° C.
5) A gelatin solution is diluted to 1%.
6) The silk fibroin solution is mixed with the gelatin solution in equal volume at 4° C., and is allowed to stand for 6 hours.
7) The mixed solution is injected into the mold having boiled-off silk tube placed therein, and frozen at −20° C. for 24 hours to obtain a silk fibroin/gelatin frozen body.
8) The frozen silk fibroin/gelatin mixture is placed into a freeze dryer, and subjected to a freeze-drying process for 48 hours to obtain a soluble silk fibroin/gelatin porous repair plug reinforced by boiled-off silk having a thickness of 5 mm.
9) The porous repair plug is placed into a vacuum dryer having water provided at the bottom, and subjected to a vacuum treatment for 6 hours to obtain a water-insoluble silk fibroin/gelatin anal fistula repair plug reinforced by boiled-off silk.

Figure 1:
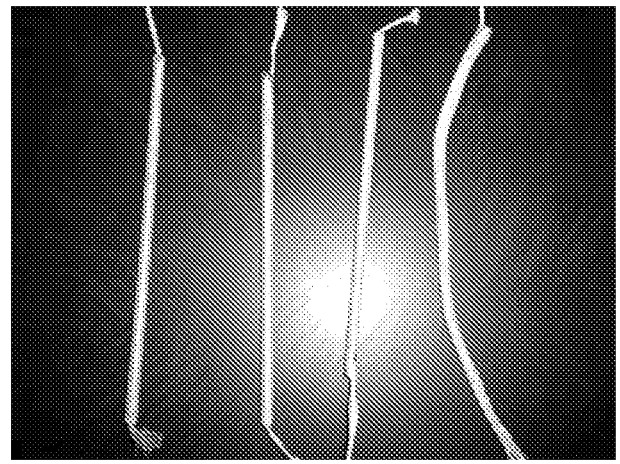
FIG. 1 is a photograph of a tubular material woven from boiled-off silk used in Example 1.
Figure 2:
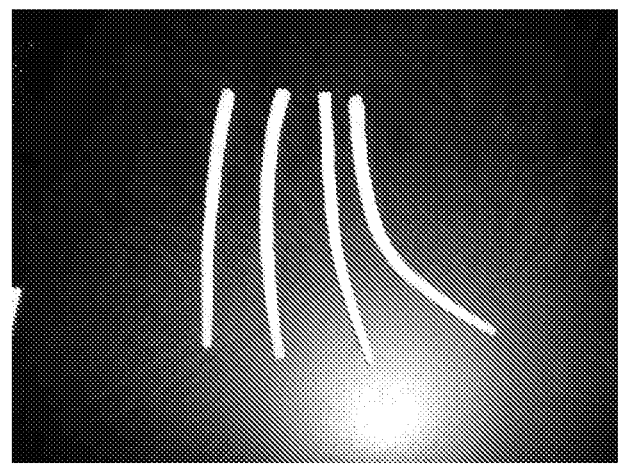
FIG. 2 is a photograph of the silk fibroin/gelatin anal fistula repair plug reinforced by boiled-off silk prepared in Example 1.

FIGS. 1 and 2 show a boiled-off silk tube having a diameter of 4 mm, and a silk fibroin/gelatin anal fistula repair plug compounded with the boiled-off silk tube, prepared according to the above method. It can be seen, the boiled-off silk is well compounded with the silk fibroin/gelatin porous material.

Figure 3:
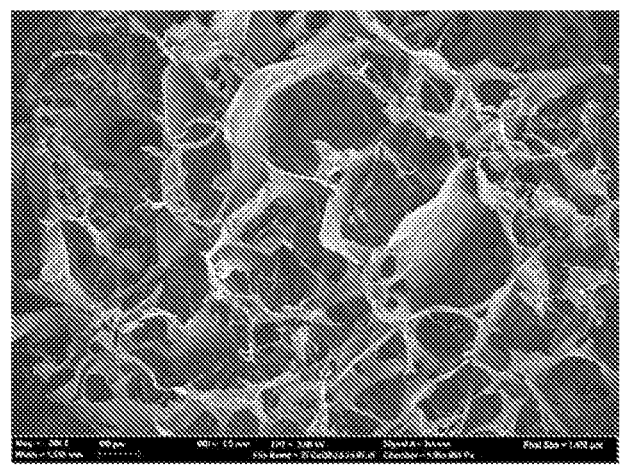
FIG. 3 is the micro porous structure of the silk fibroin/gelatin anal fistula repair plug reinforced by boiled-off silk prepared in Example 1.

FIG. 3 is a scanning electron micrograph of a silk fibroin/gelatin porous anal fistula repair plug prepared according to the above method. It can be seen, a good porous structure is formed in the material which has a pore diameter of 200-400 microns.

Figure 4:
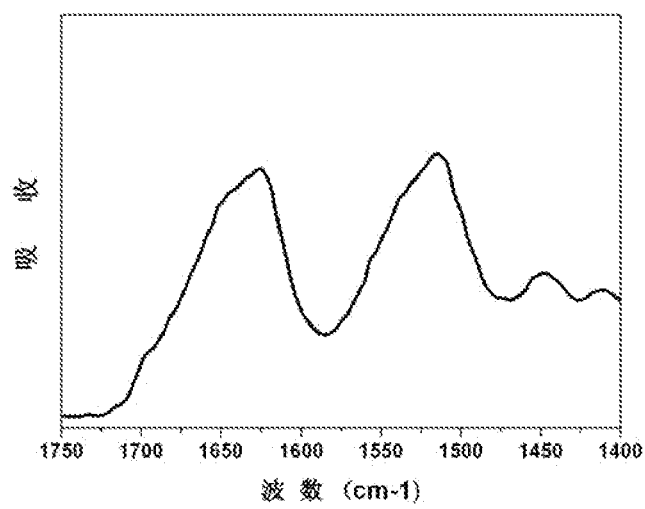
FIG. 4 is the IR spectra result of the silk fibroin/gelatin anal fistula repair plug reinforced by boiled-off silk prepared in Example 1.

FIG. 4 is the IR spectra of the silk fibroin/gelatin porous anal fistula repair plug reinforced by boiled-off silk prepared according to the above method. It can be seen, the characteristic absorption peak of the silk fibroin/gelatin porous repair plug is at 1630 cm$^{-1}$ and has a distinct shoulder peak at 1650 cm$^{-1}$, which indicates that both silk I and silk II crystalline structures exist.

Example 2

5 g of cocoons are added to 2 liters of a sodium carbonate solution having a mass concentration of 0.5%, treated at 98 to 100° C. for 40 min to remove the external sericin, and sufficiently washed to obtain pure silk fibroin.

The degummed silk fibroin (also referred to as "boiled-off silk") is woven into a tubular material having a diameter of 3 mm by a textile machine. The tubular material is placed into a conical repair plug mold having an upper diameter of 3 mm and a lower diameter of 5 mm.

The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.

The mass concentration of the silk fibroin is adjusted to 4%, and the aqueous solution is placed at 4° C. for 1 hour, such that the solution temperature is stably maintained at 4° C.

A collagen solution in acetic acid is diluted to 0.5%.

The silk fibroin solution is mixed with the collagen solution in equal volume at 4° C., and is allowed to stand for 6 hours.

The mixed solution is injected into the mold having boiled-off silk tube placed therein, and frozen at −20° C. for 24 hours to obtain a silk fibroin/collagen frozen body.

The frozen silk fibroin/collagen mixture is placed into a freeze dryer, and subjected to a freeze-drying process for 48 hours to obtain a soluble silk fibroin/collagen porous repair plug reinforced by boiled-off silk having an upper diameter of 3 mm and a lower diameter of 5 mm.

The porous repair plug is placed into a vacuum dryer having water provided at the bottom, and subjected to a vacuum treatment for 6 hours to obtain a water-insoluble silk fibroin/collagen anal fistula repair plug reinforced by boiled-off silk.

Example 3

5 g of cocoons are added to 2 liters of a sodium carbonate solution having a mass concentration of 0.5%, treated at 98 to 100° C. for 40 min to remove the external sericin, and sufficiently washed to obtain pure silk fibroin.

The degummed silk fibroin (also referred to as "boiled-off silk") is woven into a tubular material having a diameter of 4 mm by a textile machine. The tubular material is placed into a conical repair plug mold.

The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.

The mass concentration of the silk fibroin is adjusted to 4%, and the aqueous solution is placed at 4° C. for 1 hour, such that the solution temperature is stably maintained at 4° C.

A collagen solution in acetic acid is diluted to 0.5%.

The silk fibroin solution is mixed with the collagen solution in equal volume at 4° C., and is allowed to stand for 6 hours.

The mixed solution is injected into the mold having boiled-off silk tube placed therein, and frozen at −20° C. for 24 hours to obtain a silk fibroin/collagen frozen body.

The frozen silk fibroin/collagen mixture is placed into a freeze dryer, and subjected to a freeze-drying process for 48 hours to obtain a soluble silk fibroin/collagen porous repair plug reinforced by boiled-off silk.

The porous repair plug is placed into a vacuum dryer having an 80% ethanol solution provided at the bottom, and subjected to a vacuum treatment for 6 hours to obtain a water-insoluble silk fibroin/collagen porous anal fistula repair plug reinforced by boiled-off silk. This porous scaffold has a pore diameter of 200 microns or more, and a porosity of 90% or more. The main crystal structure is silk II.

Example 4

5 g of cocoons are added to 2 liters of a sodium carbonate solution having a mass concentration of 0.5%, treated at 98 to 100° C. for 40 min to remove the external sericin, and sufficiently washed to obtain pure silk fibroin.

The degummed silk fibroin (also referred to as "boiled-off silk") is woven into a tubular material having a diameter of 4 mm by a textile machine. The tubular material is placed into a conical repair plug mold.

The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.

The mass concentration of the silk fibroin is adjusted to 4%, and the aqueous solution is placed at 4° C. for 1 hour, such that the solution temperature is stably maintained at 4° C.

An aqueous gelatin solution is diluted to 0.5%.

The silk fibroin solution is mixed with the gelatin solution in equal volume at 4° C., and is allowed to stand for 6 hours.

The mixed solution is injected into the mold having boiled-off silk tube placed therein, and frozen at −20° C. for 24 hours to obtain a silk fibroin/gelatin frozen body.

The frozen silk fibroin/gelatin mixture is placed into a freeze dryer, and subjected to a freeze-drying process for 48 hours to obtain a soluble silk fibroin/gelatin porous repair plug reinforced by boiled-off silk.

The porous repair plug is placed into a vacuum dryer having an 80% methanol solution provided at the bottom, and subjected to a vacuum treatment for 6 hours to obtain a water-insoluble silk fibroin/collagen porous anal fistula repair plug reinforced by boiled-off silk. This porous scaffold has a pore diameter of 200 microns or more, and a porosity of 90% or more. The main crystal structure is silk II.

Example 5

5 g of cocoons are added to 2 liters of a sodium carbonate solution having a mass concentration of 0.5%, treated at 98 to 100° C. for 40 min to remove the external sericin, and sufficiently washed to obtain pure silk fibroin.

The degummed silk fibroin (also referred to as "boiled-off silk") is woven into a tubular material having a diameter of 3 mm by a textile machine. The tubular material is placed into a repair plug mold having an inner diameter of 2.9 mm and an outer diameter of 3.2 mm.

The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.

The mass concentration of the silk fibroin is adjusted to 4%, and the aqueous solution is placed at 4° C. for 1 hour, such that the solution temperature is stably maintained at 4° C.

A collagen solution in acetic acid is diluted to 0.5%.

The silk fibroin solution is mixed with the collagen solution in equal volume at 4° C., and is allowed to stand for 6 hours.

The mixed solution is injected into the mold having boiled-off silk tube placed therein, and frozen at −20° C. for 24 hours to obtain a silk fibroin/collagen frozen body having a thickness of 300 microns.

The frozen silk fibroin/collagen mixture is placed into a freeze dryer, and subjected to a freeze-drying process for 48 hours to obtain a soluble silk fibroin/collagen porous repair plug reinforced by boiled-off silk.

The porous repair plug is placed into a vacuum dryer having an 80% ethanol solution provided at the bottom, and subjected to a vacuum treatment for 6 hours to obtain a water-insoluble silk fibroin/collagen porous anal fistula repair plug reinforced by boiled-off silk. This porous scaffold has a pore diameter of 200 microns or more, and a porosity of 90% or more. The main crystal structure is silk II.

Example 6

5 g of cocoons are added to 2 liters of a sodium carbonate solution having a mass concentration of 0.5%, treated at 98 to 100° C. for 40 min to remove the external sericin, and sufficiently washed to obtain pure silk fibroin.

The degummed silk fibroin (also referred to as "boiled-off silk") is woven into a sheet material having an area of 4×4 cm. The sheet material is placed into a mold having a height of 4 cm.

The dried silk fibroin is dissolved into a 9.3 mol/L lithium bromide solution at about 60° C., to obtain a fibroin mixed solution. The fibroin mixed solution is added to a cellulose dialysis membrane, and dialysized with deionized water to remove lithium bromide. Thus, a pure aqueous silk fibroin solution is obtained.

The mass concentration of the silk fibroin is adjusted to 4%, and the aqueous solution is placed at 4° C. for 1 hour, such that the solution temperature is stably maintained at 4° C. The silk fibroin solution is slowly concentrated to 30%, placed at 4° C. for 3 days, and re-diluted to 4%.

The diluted silk fibroin solution is injected into the mold having boiled-off silk sheet placed therein, and frozen at −20° C. for 24 hours to obtain a silk fibroin frozen body having a height of 4 cm and an area of 4×4 cm.

The frozen body is placed into a freeze dryer, and subjected to a freeze-drying process for 48 hours to obtain a soluble silk fibroin bulk material reinforced by boiled-off silk.

The bulk material is placed into a vacuum dryer having an 80% methanol solution provided at the bottom, and subjected to a vacuum treatment for 6 hours to obtain a water-insoluble silk fibroin repair sheet material. This porous repair plug has a pore diameter of 200 microns or more, and a porosity of 90% or more. The main crystal structure is silk II.

What is claimed is:

1. A method for preparing a high-strength biological scaffold material, characterized in that, the method comprises the following steps:

boiled-off silk obtained by degumming silk is woven into a woven material by a textile machine to form a framework according to the desired shape, and then the framework is placed into a mold;

a solution containing silk fibroin is injected into the mold having the framework placed therein, and subjected to freezing and vacuum treatment; thereby a coating layer having a thickness of 100 microns to 5 cm is formed on the surface of the framework, and the high-strength biological scaffold material is prepared, wherein said solution containing silk fibroin is one selected from the group consisting of: an aqueous silk fibroin solution, a mixed solution of silk fibroin and gelatin, and a mixed solution of silk fibroin and collagen; the weave density of the woven material is such that the distance between adjacent boiled-off silks is between 0.5 mm and 3 mm, and the material of the coating layer is selected from the group consisting of: silk protein scaffold material, silk fibroin/gelatin biological scaffold material or silk fibroin/collagen biological scaffold material;

wherein the aqueous silk fibroin solution is prepared by: subjecting silk to degumming, dissolution, and dialysis to obtain a silk fibroin solution, the aqueous silk fibroin solution having a mass concentration of 0.1 to 20%; leaving the aqueous silk fibroin solution at 0 to 80° C. for 1 to 48 hours; and wherein the vacuum treatment is performed in a vacuum dryer containing water, aqueous methanol or aqueous ethanol at the bottom thereof.

2. The method for preparing a high-strength biological scaffold material according to claim 1, characterized in that, the step of coating the surface of the framework with a coating layer comprises the specific steps of:

1) preparing a solution containing silk fibroin, the solution containing silk fibroin being one selected from the group consisting of: an aqueous silk fibroin solution, a mixed solution of silk fibroin and gelatin, and a mixed solution of silk fibroin and collagen; injecting the solution containing silk fibroin into the mold having the framework placed therein, and subjecting it to freezing under a low temperature of −10 to −80° C. for 1 to 24 hours to obtain frozen crystals; freeze-drying the frozen crystals to obtain a composite material, the composite material having boiled-off silk woven material as a framework and a layer of soluble silk fibroin layer/silk fibroin and gelatin composite layer/silk fibroin and collagen composite layer coated on the framework;

2) placing the composite material obtained in step 1) into a vacuum dryer and performing a vacuum treatment for 20 minutes to 24 hours to obtain a water-insoluble composite high-strength biological scaffold material, the composite high-strength biological scaffold material having boiled-off silk woven material as a framework and a coating layer provided on the framework, the material of the coating layer being selected from the group consisting of: silk protein scaffold material, silk fibroin/gelatin biological scaffold material or silk fibroin/collagen biological scaffold material; and the vacuum dryer containing water, aqueous methanol or aqueous ethanol at the bottom thereof;

wherein the mixed solution of silk fibroin and gelatin is prepared by: preparing an aqueous gelatin solution by adding medical gelatin into distilled water, heating to obtain an aqueous gelatin solution, and leaving the solution at 0 to 10° C. for 30 minutes to 2 hours, the aqueous gelatin solution having a mass concentration of 0.01 to 20%; then mixing an aqueous silk fibroin solution with the aqueous gelatin solution at a mass ratio of silk fibroin to gelatin of 100:2 to 20, to obtain the mixed solution of silk fibroin and gelatin;

the mixed solution of silk fibroin and collagen is prepared by: preparing an aqueous silk fibroin solution by subjecting silk to degumming, dissolution, and dialysis to obtain a silk fibroin solution, the aqueous silk fibroin solution having a mass concentration of 0.1 to 20%; leaving the aqueous silk fibroin solution at 0 to 80° C. for 1 to 48 hours; preparing a solution of collagen in acetic acid at a concentration of 0.01% to 2%, and leaving the solution at 0 to 10° C. for 30 minutes to 2 hours; then mixing the aqueous silk fibroin solution with the solution of collagen in acetic acid at a mass ratio of silk fibroin to collagen of 100:2 to 20, to obtain the mixed solution of silk fibroin and collagen.

3. The method for preparing a high-strength biological scaffold material according to claim 2, wherein the material is in a shape of an anal fistula repair plug, characterized in that, the method comprises the following steps:

1) preparing a solution containing silk fibroin, the solution containing silk fibroin being one selected from the group consisting of: an aqueous silk fibroin solution, a mixed solution of silk fibroin and gelatin, and a mixed solution of silk fibroin and collagen;

2) weaving degummed boiled-off silk into a tubular material to provide a framework and placing the tubular material into a mold for preparing anal fistula repair plug, the weave density of the tubular material being such that the distance between adjacent boiled-off silks is between 0.5 mm and 3 mm;

3) injecting the solution containing silk fibroin into the mold having the tubular material placed therein, and subjecting it to freezing under a low temperature of −10 to −30° C. for 20 to 24 hours to obtain a frozen body; freeze-drying the frozen body to obtain a soluble composite anal fistula repair plug, the soluble composite anal fistula repair plug having the tubular material woven from boiled-off silk as a framework and a layer of soluble silk fibroin layer/silk fibroin and gelatin composite layer/silk fibroin and collagen composite layer coated on the framework;

4) placing the soluble composite anal fistula repair plug into a vacuum dryer and performing a vacuum treatment for 4 hours or more to obtain a water-insoluble composite anal fistula repair plug, the water-insoluble composite anal fistula repair plug having the tubular material woven from boiled-off silk as a framework and a biological scaffold material as a coating layer, the biological scaffold material being selected from the group consisting of: silk protein biological scaffold material, silk fibroin/gelatin biological scaffold material or silk fibroin/collagen biological scaffold material, the framework being embedded inside the coating layer;

wherein in step 1), the aqueous silk fibroin solution is prepared by: preparing an aqueous silk fibroin solution having a mass concentration of 0.5% to 5% by a conventional method, and leaving the aqueous silk fibroin solution at 0 to 10° C. for 30 minutes or more;

the mixed solution of silk fibroin and gelatin is prepared by: preparing an aqueous gelatin solution having a mass concentration of 0.05% to 1%, and leaving the solution at 0 to 10° C. for 30 minutes to 2 hours; mixing an aqueous silk fibroin solution with the aqueous gelatin solution uniformly such that the mass concentration of silk fibroin is 0.2% to 3% and the mass concentration of gelatin is 0.02% to 0.2% upon mixing; and leaving the mixture stand for 4 to 10 hours to obtain the mixed solution of silk fibroin and gelatin;

the mixed solution of silk fibroin and collagen is prepared by: preparing a solution of collagen in acetic acid at a concentration of 0.05% to 1%, and leaving the solution at 0 to 10° C. for 30 minutes to 2 hours; mixing an aqueous silk fibroin solution with the solution of collagen in acetic acid uniformly at 0 to 10° C. such that the mass concentration of silk fibroin is 0.2% to 3% and the mass concentration of collagen is 0.02% to 0.2% upon mixing; and leaving the mixture stand for 4 to 10 hours to obtain the mixed solution of silk fibroin and collagen.

4. The method for preparing the high-strength anal fistula repair plug according to claim 3, characterized in that, in step 4), the coating layer has a thickness of 100 microns to 5 mm; and the biological scaffold material has a pore size of 200 to 400 microns, and a porosity of 80% or more.

\* \* \* \* \*